United States Patent
Jaeger et al.

(10) Patent No.: US 6,174,278 B1
(45) Date of Patent: Jan. 16, 2001

(54) IMPLANTABLE MICROPHONE

(75) Inventors: Eric Jaeger, Redwood City; Jerod Goldstein, Soquel; Harry S. Robbins, Saratoga, all of CA (US)

(73) Assignee: Symphonix Devices, Inc., San Jose, CA (US)

( * ) Notice: Under 35 U.S.C. 154(b), the term of this patent shall be extended for 0 days.

(21) Appl. No.: 09/222,257

(22) Filed: Dec. 28, 1998

Related U.S. Application Data (62) Division of application No. 08/826,303, filed on Mar. 27, 1997, now Pat. No. 5,888,187.

(51) Int. Cl.⁷ ........................................................ A61F 5/58
(52) U.S. Cl. ............................................................. 600/23
(58) Field of Search ............................ 381/70, 23; 600/23, 600/25, 483, 484, 514, 823, 528, 529, 586; 607/55–57, 136, 137; 424/112, 116, 185

(56) References Cited

U.S. PATENT DOCUMENTS

| | | |
|---|---|---|
| 2,702,354 | 2/1955 | Chropening . |
| 3,736,436 | 5/1973 | Crites . |
| 4,198,542 | 4/1980 | Ducommun . |
| 4,343,969 | 8/1982 | Kellett . |
| 4,473,905 | 9/1984 | Katz et al. . |
| 4,524,247 | 6/1985 | Lindenberger et al. . |
| 4,539,699 | 9/1985 | Katz et al. . |
| 4,547,894 | 10/1985 | Benson et al. . |
| 4,571,739 | 2/1986 | Resnick . |
| 4,591,668 | 5/1986 | Iwata . |
| 4,672,673 | 6/1987 | Katz et al. . |
| 4,685,448 | 8/1987 | Shames et al. . |
| 4,691,360 | 9/1987 | Bloomfield, III . |
| 4,706,292 | 11/1987 | Torgeson . |
| 4,821,326 | 4/1989 | MacLeod . |
| 5,085,628 | 2/1992 | Engebretson et al. . |
| 5,275,159 | 1/1994 | Griebel . |
| 5,326,349 | 7/1994 | Baraff . |
| 5,456,654 | 10/1995 | Ball . |
| 5,554,096 | 9/1996 | Ball . |

OTHER PUBLICATIONS

Debreceni et al., "An Implantable Electromagnetic Sound Source for Speech Productin", vol. XXIII, Trans. Am. Soc. Artif. Itern, Organs, 1977. pp. 22–26.*

(List continued on next page.)

Primary Examiner—Samuel G. Gilbert
(74) Attorney, Agent, or Firm—Medlen & Carroll, LLP (57) ABSTRACT

The present invention is directed to methods for amplifying vocal (i.e., speech) and other sounds produced by humans and other animals. The present invention provides implantable microphones and sound amplification systems suitable for use in diagnostic and research settings, as well as for use by subject's in need of assistance to vocalize.

21 Claims, 8 Drawing Sheets

OTHER PUBLICATIONS

Otto et al., "Electrophysiologic pacing of vocal cord abductors in bilateral recurrent laryngeal nerve paralysis," *Am. J. Surg.* 150:447–451 [1985].

Broniatowski et al., "Laryngeal pacemaker. Part I. Electronic pacing of reinnervated strap muscles in the dog," *Otolaryngol. Head Neck Surg.* 94:41–44 [1986].

Broniatowski et al., "Laryngeal pacemaker. II. Electronic pacing of reinnervated posterior cricoarytenoid muscles in the canine," *Laryngoscope* 95:1194–1198 [1985].

Otto et al., "Coordinated electrical pacing of vocal cord abductors in recurrent laryngeal nerve paralysis," *Otolaryngol. Head Neck Surg.* 93:634–638 [1985].

McRae and Pillsbury, "A modified intraoral electrolarynx," *Arch. Otolaryngol.* 105:360–361 [1979].

Ohno, "The Implantable Hearing Aid Part I," *Audecirel Fall*, pp. 28–30 (1984).

Yanagihara et al., "Development of an implantable hearing aid using a piezoeiectric vibrator of bimorph design: State of the art," *Otolaryngology Head and Neck Surgery* 92(6):706–712 (1984).

Suzuki et al., "Early Studies and the History of Development of the Middle Ear Implant in Japan," *Adv. Audiol.* 4:1–14 (1988).

Deddens et al., "Totally Implantable Hearing Aids: The Effects of Skin Thickness on Microphone Function," *Am. J. Otolaryngol.* 12:1–4 (1990).

Rion Co., Ltd., "Middle Ear Implant Information".

Knorr and Zwitman, "The Design of a Wireless–Controlled Intra–Oral Electrolarynx," *J. Bioeng.* 1:165–171 (1977).

Schellin et al., "Corona–poled piezoelectric polymer layers of P(VDF/TrFE) for micromachined silicon microphones," *J. Micromech. Microeng.* 5:106–108 (1995).

Scheeper et al., "Improvement of the performance of microphones with a silicon nitride diaphragm and backplate," *Sensors and Actuators A*, 40:179–186 (1994).

Otto and Davis, "Functional electrical stimulation for the treatment of bilateral recurrent laryngeal nerve paralysis," *Otolaryngology—Head and Neck Surgery* 95(1):47–51 (1986).

Broniatowski, "Bionic Larynx: Electronic Control of the Reimplanted Organ in the Dog," *Laryngoscope* 98:1107–1115 (1988).

Guyton, "Functions of the Respiratory Passageways: Functions of the Nose," *Textbook of Medical Physiology, Sixth Edition*, W.B. Saunders Company, Philadelphia, pp. 486–489 (1981).

Gray, Anatomy, *Descriptive and Surgical*, 1901 Edition, (eds. Pick and Howden), Running Press, Philadelphia, pp. 750–753, 955–969 (1974).

* cited by examiner

IMPLANTABLE MIC RESPONSE IN MODEL VS AP MIC RESPONSE IN AIR

IMPLANTABLE MICROPHONE

This is a Divisional of application Ser. No. 08/826,303 filed on Mar. 27, 1997, now U.S. Pat. No. 5,888,187, issued Mar. 30, 1999.

FIELD OF THE INVENTION

The present invention relates to the field of devices and methods for improving sound production and amplification in vocally impaired persons and particularly to the field of implantable microphones. The present invention also provides devices and methods for improving sound production and amplification suitable for diagnostic purposes.

BACKGROUND OF THE INVENTION

Figure 1A:
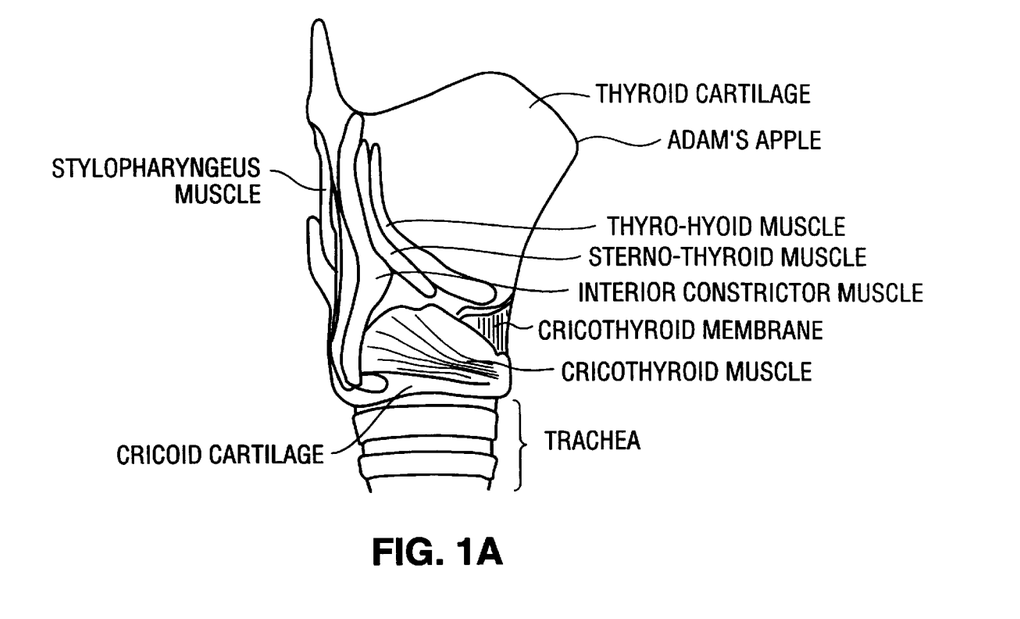
FIG. 1 is a vertical cross-section diagram of the larynx and upper part of the trachea.
Figure 1B:
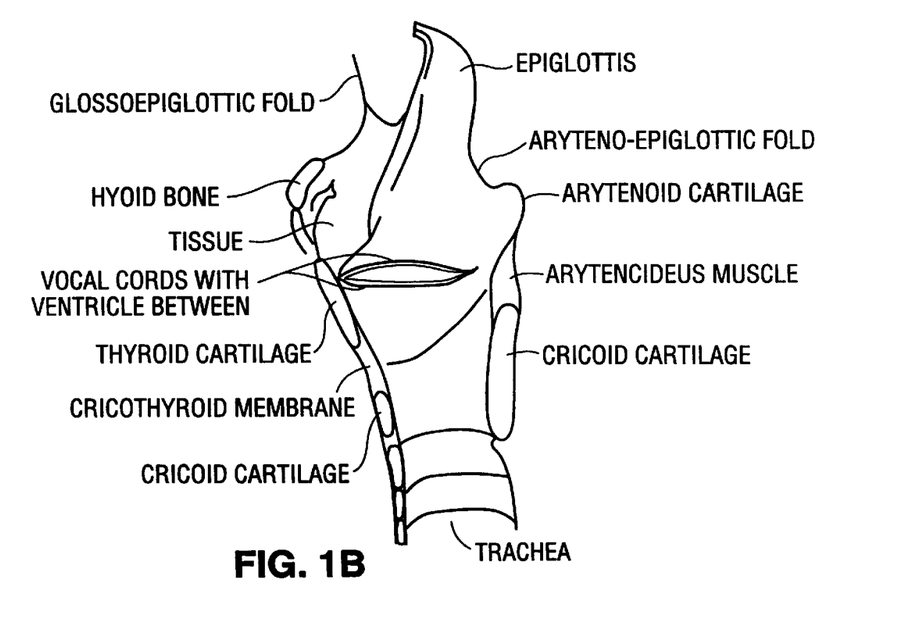

The production of vocal sounds (e.g., speech) involves the respiratory system, as well as speech control centers in the cerebral cortex, respiratory centers of the brain stem, and the articulation and resonance structures of the mouth, nasal and chest cavities. However, the "organ of voice" is the larynx, a specially adapted organ located in the upper air passageway. The larynx is in the form of a triangular box, with the back and sides flattened, and a prominent vertical ridge in front; the top is broader than the bottom. Simple diagrams of the larynx are shown in FIG. 1 (FIG. 1A is a side view, and 1B is a vertical cross-section of the larynx and upper trachea). The larynx is composed of cartilages connected together by ligaments and numerous muscles; it is lined by mucous membrane that is continuous with the mucous membrane lining of the pharynx and the trachea. The vocal cords are folds located along the lateral walls of the larynx, that are stretched and positioned by several muscles. There are nine cartilages in the larynx (i.e., the thyroid, cricoid, epiglottis, and two each of arytenoid, corniculate, and cuneiform). The thyroid cartilage is the largest cartilage of the larynx, consisting of two lateral lamellae that are united at an acute angle in front, to form a vertical projection in the mid-line (i.e., the "Adam's apple").

During speech, various laryngeal muscles move the vocal cords within the lateral laryngeal walls. When the vocal cords are brought together and air is expired, air pressure from below (i.e., the lower respiratory tract) first pushes the vocal cords apart, allowing rapid flow of air between their margins. The rapid flow of air then immediately creates a partial vacuum between the vocal cords, pulling them together once again. This stops the air flow, builds up pressure behind the cords, and the cords open once more, in order to continue the vibratory pattern. For normal respiration, the muscles pull laryngeal cartilages forward and apart. Contractions of the many small slips of muscle comprising the thyroarytenoid muscles control the shape of the vocal cords (i.e., thick or thin, with sharp or blunt edges), during different types of phonation. The pitch of the emitted sound can be changed by either stretching or relaxing the vocal cords, or the shape and mass of vocal cord edges. The muscles attached to the external surfaces of the larynx can pull against the cartilages, thereby helping to stretch or relax the vocal cords. For example, the entire larynx is moved upward by the external laryngeal muscles, stretching the vocal cords for production of very high frequency sounds, and larynx is moved downward (i.e., the vocal cords are loosened) for production of very bass (i.e., low frequency) sounds.

Laryngeal function may be compromised due to various causes, including upper airway obstruction, paralysis, laryngectomy, etc. Partial upper airway (i.e., the passageway from the posterior pharynx to the distal trachea) obstruction is a potentially serious condition, as the individual may lack sufficient respiratory capacity for unaided respiration or speech. Obstruction may be caused by numerous conditions, including extrinsic compression (e.g., mediastinal neoplasm, retrosternal goiter, retropharyngeal abscess, fibrosing mediastinitis, or thoracic aortic aneurysm), intraluminal obstruction (e.g., foreign body aspiration), intrinsic structural abnormalities caused by infectious diseases (e.g., epiglottitis, croup, leprosy, syphilis, and diphtheria), neoplastic disorders (e.g., oropharyngeal, laryngeal, and tracheal tumors), inflammatory and degenerative disorders (e.g., enlarged tonsils and adenoids, laryngeal or tracheal granulation tissue, cricoarytenoid arthritis, tracheobronchial amyloidosis, sarcoidosis, laryngomalacia, tracheomalacia, tracheal or laryngeal stenosis, and relapsing polychondritis), or neurologic disorders (e.g., bilateral vocal cord paralysis and functional laryngospasm).

Bilateral recurrent laryngeal nerve paralysis resulting in airway compromise is commonly encountered by otolaryngologists. Often, it is a result of thyroidectomy, although other causes (e.g., idiopathic, neurogenic, and traumatic). Traditionally, patients with bilateral recurrent laryngeal nerve paralysis were surgically treated by tracheostomy (i.e., creation of an opening into the trachea though the neck, with the tracheal mucosa being brought into continuity with the skin; the term is also used in reference to the opening, as well as in reference to a tracheotomy done for insertion of a tube to relieve upper airway obstruction or to facilitate ventilation).

Tracheostomy provides a proper airway and maintains some voice. However, this solution has been less than ideal, as most of the procedures sacrifice voice for the airway. Other treatment approaches, such as recurrent nerve decompression, exploration and neurorrhaphy (i.e., suture of a divided nerve), the nerve and muscle pedicle procedure, and various neural reanastamosis procedures have also been attempted, although they have also only achieved limited success. (See e.g., Otto et al., "Electrophysiologic pacing of vocal cord abductors in bilateral recurrent laryngeal nerve paralysis," Am. J. Surg., 150:447–451 [1985]). Reanastomosis of severed recurrent laryngeal nerves usually fails or is unsatisfactory; tracheotomy is unsightly, non-physiologic, and often followed by long-term complications; arytenoidectomy is often complicated by aspiration, and always results in dome diminution of voice; and nerve-muscle pedicles are sometimes successful, although the impaired airway is not always satisfactorily restored. As stated by Otto et al., "[i]t is apparent that an adequate physiologic solution is yet to be found, and the original dilemma remains unsolved, that is, improving the airway worsens voice quality and may result in aspiration. The ideal solution would be to restore an adequate airway, preserve normal phonation, and preserve the protective function of the vocal cords, thus preventing aspiration." (Otto et al., supra, at 447). These sentiments are oft-repeated in the literature dealing with rehabilitation of patients with bilateral vocal cord paralysis. (See e.g., Broniatowski et al., "Laryngeal pacemaker. Part I. Electronic pacing of reinnervated strap muscles in the dog," Otolaryngol. Head Neck Surg., 94:41–44 [1986]; Broniatowski et al., "Laryngeal pacemaker. II. Electronic pacing of reinnervated posterior cricoarytenoid muscles in the canine," Laryngoscope 95:1194–1198 [1985]); and Otto et al., "Coordinated electrical pacing of vocal cord abductors in recurrent laryngeal nerve paralysis," Otolaryngol. Head Neck Surg., 93:634–638 [1985]).

Other situations in which voice and/or ventilation are compromised include patients who have undergone laryngectomy, due to cancer or other causes. In order to speak, these patients must use sign language, writing, esophageal speech, or use a device. Various devices have been developed in order to assist these patients, including electrolaryngeal and other devices to generate speech. (See e.g., U.S. Pat. Nos. 4,473,905, 4,672,673, 4,550,427, and 4,539,699 to Katz et al.; U.S. Pat. No. 4,547,894 to Benson et al.; U.S. Pat. No. 5,326,349 to Baraff; U.S. Pat. No. 4,821,326 to MacLeod; U.S. Pat. No. 4,706,292 to Torgeson; U.S. Pat. No. 4,691,360 to Bloomfield, Ill; and U.S. Pat. No. 4,571,739 to Resnick; all of which are incorporated by reference). However, many electrolarynx devices are designed to be hand-held, presenting obstacles to post-laryngectomy patient who cannot develop esophageal speech, and requires the use of both hands. In addition, such devices as the pneumatic larynx, which requires that the patient have sufficient respiratory capacity to make the device function. Development of alternative methods, such as the intraoral electrolarynx has represented an improvement. However, saliva can obstruct the intraoral larynx. Other devices include the extralaryngeal electrolarynx, which is of limited value to those patients with considerable post-radiation fibrosis of the neck. In yet another device, the transducer and intraoral tubing are attached to eyeglass frames, the activating switch is strapped to the medial aspect of the upper arm, and the power pack is carried in the pocket of a shirt or jacket. (See e.g., McRae and Pillsbury, "A modified intraoral electrolarynx," Arch. Otolaryngol., 105:360–361 [1979]).

It is clear that improved means for providing speech to patients with vocal cord abnormalities, laryngeal paralysis, or laryngectomy are needed.

SUMMARY OF THE INVENTION

The present invention relates to the field of devices and methods for improving sound production and amplification in vocally impaired persons and particularly to the field of implantable microphones. The present invention also provides devices and methods for improving sound production and amplification suitable for diagnostic purposes.

The present invention provides two-stage implantable microphone devices and methods for their use. In one embodiment, the implantable microphone of the present invention has stages that allow selection of the microphone frequency response and sensitivity. The implantable microphones of the present invention provide excellent audio characteristics and are very thin, making them particularly suited for implantation.

In one embodiment, the present invention provides an implantable microphone device comprising a housing, including a diaphragm, the housing and diaphragm enclosing a chamber; a microphone coupled to the housing; and a vent connecting the microphone to the chamber, so that vibrations of the diaphragm are transmitted through the chamber and vent to the microphone. In a preferred embodiment, the transducer in the microphone is an electret microphone. In other embodiments, the transducer is piezo or electromagnetic. Thus, it is not intended that the present invention be limited to any particular transducer included within the microphone.

In an alternative embodiment, the present invention provides an implantable microphone device comprising, a housing, including a diaphragm, the housing and diaphragm enclosing a chamber; an acoustic resistor between the diaphragm and an opposing surface of the housing; a microphone coupled to the housing; and a vent connecting the microphone to the chamber, so that vibrations of the diaphragm are transmitted through the chamber and vent to the transducer.

In yet another embodiment, the present invention provides an implantable microphone device comprising a housing, including a diaphragm, the housing and diaphragm enclosing a chamber; a microphone coupled to the housing; and a vent connecting the microphone to the chamber so that vibrations of the diaphragm are transmitted through the chamber and vent to a surface of the microphone.

In a further embodiment, the present invention provides an implantable microphone device, comprising a housing, including a diaphragm having a plurality of bellows, the housing and diaphragm enclosing a chamber; an acoustic resistor between the diaphragm and an opposing surface of the housing; a microphone coupled to the housing; and a vent connecting the microphone to the chamber so that vibrations of the diaphragm are transmitted through the chamber and vent to the microphone.

The present invention also provides methods for amplifying speech comprising the steps of providing a subject, and an implantable microphone for producing an electronic signal responsive to the subject's vocalizations; and implanting the implantable microphone within the subject.

In one embodiment of the method of the present invention, the method comprises the step of providing a subject, an implantable microphone for producing an electronic signal responsive to the subject's vocalizations, an amplifying means for amplifying the electronic signal to produce an amplified signal, and a broadcasting means for broadcasting the amplified signal to produce a broadcasted signal.

In an alternative embodiment, the amplifying means further comprises a filtering means. In yet another embodiment, the amplifying means further comprises a processing means. In a preferred embodiment, the method of the present invention further comprises a modulating means, wherein the amplified signal is modulated; and a demodulating means, wherein the broadcasted signal is demodulated. It is contemplated that the modulated signal is selected from the group consisting of AM, FM, and bass band. In an alternative preferred embodiment, the broadcasting means is comprised of a transmitter coil, a receiving coil, an amplifier, and at least one speaker. In a particularly preferred embodiment, the transmitter coil is implanted within the subject, and the receiving coil may be external or surgically implantable within the subject.

In some embodiments, the speaker is a room speaker, while in others, the speaker is a personal speaker. In preferred embodiments of the method as it is used to assist vocally-impaired subjects, implantable microphone is implaned in close proximity to the subject's vocal cords. In particularly preferred embodiments, the implanted microphone is hermetically sealed.

The present invention also provides methods for monitoring body function, comprising the step of: providing a subject, an implantable microphone for producing an electronic signal responsive to the subject's body functions, and implanting the microphone within the subject.

In preferred embodiment, the methods for monitoring body function, comprising the step of: providing a subject, an implantable microphone for producing an electronic signal responsive to the subject's body functions, an amplifying means for amplifying the electronic signal to produce an amplified signal, and a broadcasting means for broadcasting the amplified signal to produce a broadcasted signal; implanting the implanted microphone within the subject; and monitoring the implanted microphone.

In one embodiment, the amplifying means further comprises a filtering means. In alternative embodiments, the amplifying means further comprises a processing means. In preferred embodiments, the method further comprises a modulating means, wherein the amplified signal is modulated; and a demodulating means, wherein the broadcasted signal is demodulated. It is contemplated that various modulated signals will be used in the present invention, including but not limited to the group consisting of FM, AM, and bass band. In alternatively preferred embodiments, the broadcasting means is comprised of a transmitter coil, a receiving coil, an amplifier, and at least one speaker. In particularly preferred embodiments, the transmitter coil is implanted within the subject, and the receiving coil may be external or implanted within the subject. In an alternative embodiment, the speaker is a room speaker, while in other alternative embodiments, the speaker is a personal speaker. In particularly preferred embodiments, the broadcasted signal is recorded.

It is contemplated that the method of the present invention will be used to monitor various body functions, including, but not limited to heart rate, respiration, and intestinal movement. It is further contemplated that the present invention will be used for diagnostic purposes, to determine whether a subject is suffering from disease or any other pathological condition.

It is further contemplated that the subject be human, although it is also contemplated that the present invention will be used with non-human animals for monitoring, as well as diagnostic purposes.

DESCRIPTION OF THE INVENTION

The present invention relates to the field of devices and methods for improving sound production and amplification in vocally impaired persons and particularly to the field of implantable microphones. The present invention also provides devices and methods for improving sound production and amplification suitable for diagnostic purposes.

In one embodiment, the present invention provides an implantable microphone that is surgically placed in the oral cavity (e.g., in the larynx or close to the vocal cords) of vocally-impaired persons. It is contemplated that a vocal stimulator will be used in conjunction with the present invention. It is further contemplated that laryngectomy patients will use the present invention to amplify esophageal speech. Thus, it is intended that the present invention be utilized either alone (i.e., without the implementation of any additional devices) or in conjunction with other methods and/or devices for improving and/or amplifying speech of vocally-impaired subjects.

Figure 8:
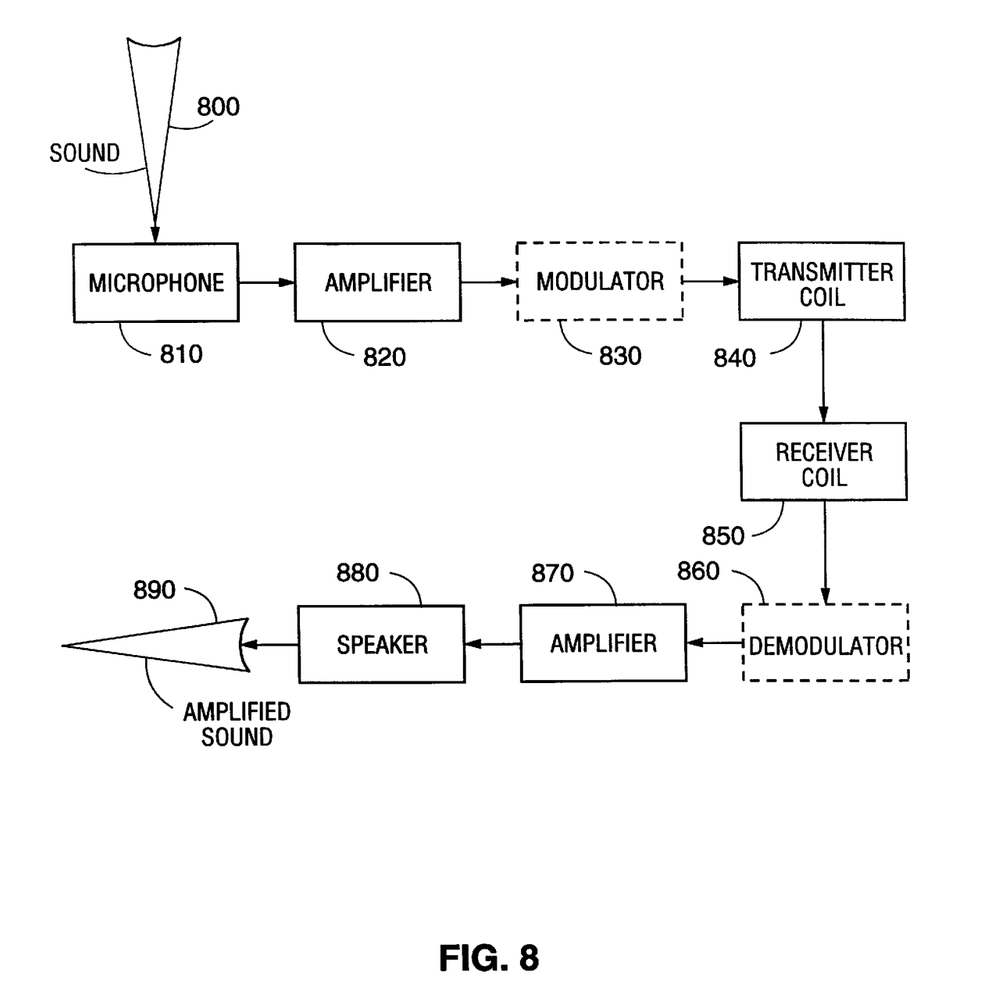
FIG. 8 is a schematic showing the various components of the present invention.

When the person speaks, the microphone signal is sent to an electronics package located within the vocal electronics package. This electronics package processes the microphone signal by shaping or altering the frequency response and amplifies the resultant signal. The processed signal is then sent to a transmitter coil, from which it is broadcast in FM, AM or other frequencies. The transmitter coil may be placed at various locations, including as an implant placed within the patient. A second receiver (amplifier)/speaker system is then used to amplify the signal, so that the person's voice can be heard loudly and clearly by an audience or listener. In one embodiment, the second amplifier transmits to a room amplification system, while in other embodiments, the second amplifier transmits to a personal speaker (i.e., a speaker that is worn by the patient). FIG. 8 is a schematic of one embodiment of the implantable microphone system. In this Figure, the modulator (830) and demodulator (860) are optional (i.e., in some embodiments the modulator and demodulator are included, while in others they are not). In this embodiment, the microphone (810), picks up the sound (800) produced by the patient and converts it to an electrical signal, and transmits to an amplifier (820), which, in some embodiments, contains means for processing and/or filtering the signal, and transmits it to a transmitter coil (840) that picks up the signal from the modulator or amplifier, and broadcasts it to a receiver coil (850). In preferred embodiments, the transmitter coil (840) is implanted, while the receiver coil (850) is external. The receiver coil (850) then transmits the signal to a demodulator (860), if one is included, or another amplifier (870), which amplifies the signal to produce amplified sound (890) that is produced by at least one speaker (880). These elements are described in more detail below.

In preferred embodiments, the electronics package in the second receiver/speaker system is designed to receive, demodulate, and/or surge-protect signals. The circuit package is comprised of a machined, formed or drawn titanium (preferred), or any other biocompatible metal or ceramic housing, that is configured with a space large enough to house electronic circuitry. The electronic circuitry is built on ceramic (preferred), polyimide, or printed circuit board technology, and contains active and/or passive electronic components. The active and/or passive electronic components may be configured to act as a receiver, when coupled with receiving antenna or coil. In alternative embodiments, it is configured to act as a demodulation circuit, thereby separating the signal of interest from the carrier signal used to facilitate transmission. In still further embodiments, the circuit is configured to provide surge protection from received signals, insuring that the maximum amplitude of any signal does not exceed a predetermined value.

Figure 3:
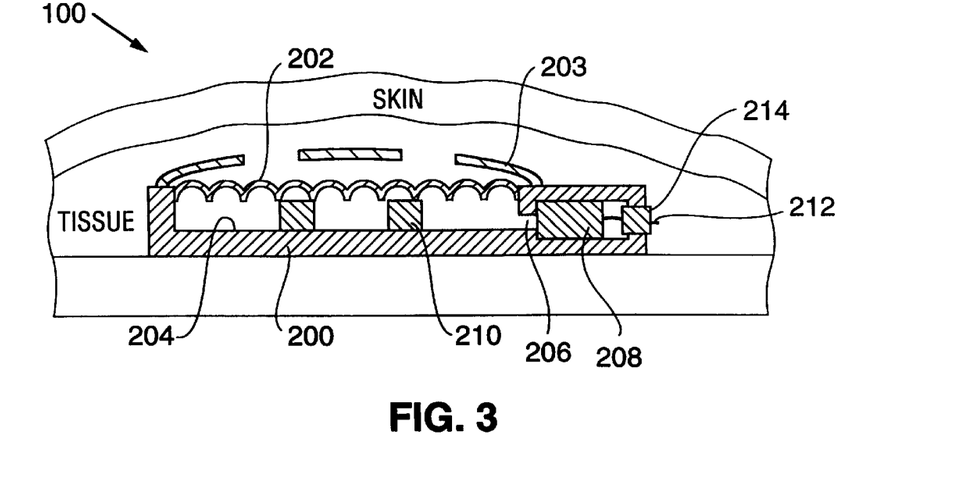
FIG. 3 shows a cross-sectional view of a two-stage implantable microphone.

In some embodiments, once the electronic circuitry is placed within the housing, the inputs and outputs of the circuit are connected to hermetically-sealed feedthroughs that exit the housing as required. These hermetically sealed feedthroughs are comprised of biocompatible materials (e.g., gold, ceramic, platinum, etc.). The feedthrough insulator is comprised of a biocompatible dielectric, preferably, ceramic, sapphire, or glass alloy. The electrical conductor pin is comprised of a biocompatible metal or alloy (preferably platinum or platinum alloy). The pin, insulator, and housing are hermetically sealed with a biocompatible noble metal (preferably gold). The sealing process may be initiated using heat (e.g., brazing or laser). In one embodiment, the housing containing the electronic circuitry is itself hermetically sealed (e.g., by brazing or welding) a lid or closure on the housing, thereby completely sealing off the electronics from the outside environment. FIG. 3 shows a cross-sectional view of one embodiment of a two-stage implantable microphone useful in the present invention.

Figure 2:
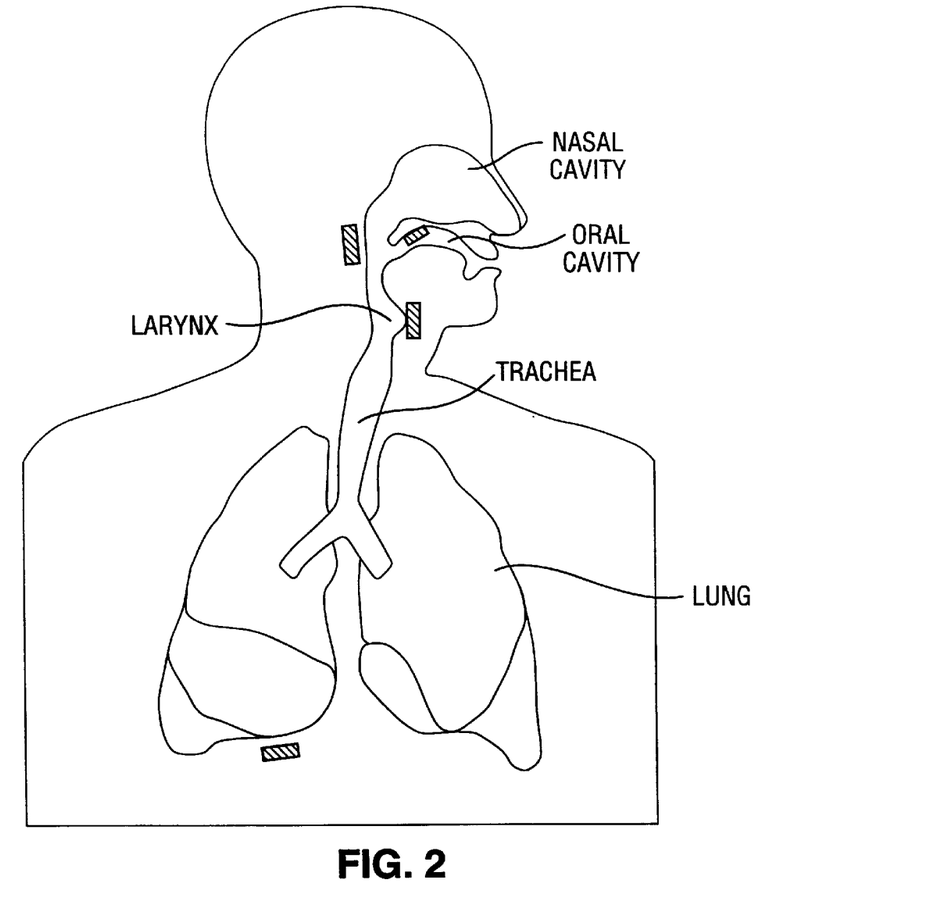
FIG. 2 illustrates various locations in which the implantable microphone may be placed.

As shown in FIG. 2, in this embodiment of the present invention, the implantable microphone is located under the skin, and within underlying tissues, such as the larynx or oral cavity. In this Figure, the shaded rectangular boxes represent the microphone. In alternative embodiments, the implantable microphone is attached to the cartilage, although in other embodiments, the implantable microphone is attached to bone (i.e., through use of bone screws to secure the microphone to the bone), surgically placed into a pocket composed of tissue, or surgically adhered to any structure suitable for the purpose. A shock absorbent material (e.g., silicone or polyurethane) may be placed between the implantable microphone and the cartilage, for vibration isolation. It is contemplated that the implanted microphone be placed in various locations, for example, it may be implanted anywhere within the nasopharyngeal cavity, laryngopharynx, throat, or larynx.

The implantable microphone includes a housing (200) and a diaphragm (202). In preferred embodiments, the diaphragm is somewhat flexible. In alternate preferred embodiments, the diaphragm and housing both include titanium and are laser welded together. In other embodiments, the housing may include ceramic material, and the diaphragm may include gold, platinum, or stainless steel. In order to promote flexibility, the diaphragm may include bellows or ridges.

In particularly preferred embodiments, the implantable microphone includes a protective cover (203). The protective cover protects the implantable microphone and diaphragm from damage (i.e., during accidental damage to the throat area). The protective cover includes inlet ports which allow sounds to travel to the diaphragm. The protective cover may comprise a number of materials, including titanium and ceramic.

In one embodiment, the housing and diaphragm enclose a chamber (204), which includes a gas (e.g., oxygen, argon, helium, nitrogen, etc.). A vent (206) is connected to the chamber, and allows vibrations of the diaphragm to be transmitted through the chamber and vent to a transducer (208). In a preferred embodiment, the microphone is a commercially available electret condenser microphone (Knowles). However, it is intended that various microphone embodiments will be useful in the present invention. For example, it is intended that implantable microphones are components of other implantable devices, such as implantable electromagnetic hearing transducers. (See e.g., U.S. Pat. Nos. 5,554,096 and 5,456,654 to Ball; and U.S. Pat. No. 5,085,628 to Engebretson et al. all of which are herein incorporated by reference, will be used, or modified as necessary to use in embodiments of the present invention.)

It is further contemplated that other devices, such as the electret pressure transducer disclosed by Crites in U.S. Pat. No. 3,736,436, herein incorporated by reference, as well as the integrated electroacoustic transducer of Lindenberger et al., (U.S. Pat. No. 5,524,247, herein incorporated by reference), and the microphones disclosed by Iwata (U.S. Pat. No. 4,591,668, herein incorporated by reference), and Creed et al. (U.S. Pat. No. 2,702,354, herein incorporated by reference) can be used or modified as necessary for use in various embodiments of the present invention.

The chamber and vent form two stages through which sounds pass from the diaphragm to the transducer microphone. By increasing the surface area of the diaphragm that generates sound waves, and increasing the surface area of the microphone that receives the sound waves, the sensitivity of the implantable microphone can be enhanced. In order to maximize the surface area of the diaphragm, yet keep the implantable microphone thin, the chamber is defined or enclosed by the diaphragm and an opposing side of the housing. The configuration of the microphone allows the implantable microphone to be extremely sensitive, yet very thin, an important consideration for implantable devices.

The frequency response and sensitivity of the implantable microphone may be controlled by the selection of the relative chamber and vent volumes, among other factors (e.g., the selection of the microphone). In less preferred configurations, the sealed chamber may set up standing resonance and interference patterns, resulting in the production of resonant wave production (e.g., the "sea shell effect"). Accordingly, an acoustic resistor (210) may be placed within the chamber between the diaphragm and the opposing sides of the housing. The acoustic resistor may be composed of any resilient material, including but not limited, to anti-static open cell foam, and porous foam rubber.

Sound waves passing through the chamber and vent generate vibrations on a surface of the microphone (208). The microphone transforms these vibrations into electrical signals (i.e., the microphone is a transducer). Leads (212) from the microphone pass through a plate (214). In preferred embodiments, the plate, along with the diaphragm/housing junctions hermetically seal the implantable microphone.

Figure 4:
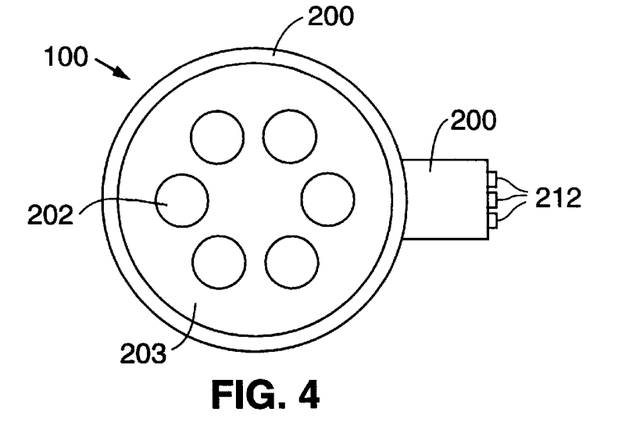
FIG. 4 shows a top view of one embodiment of a two-stage implantable microphone.

FIG. 4 shows a top view of one embodiment of a two-stage implantable microphone. As shown, the protective cover (203), and the underlying diaphragm comprises the majority of the top surface area of the implantable microphone. There are six inlet ports through which sound may travel to the underlying diaphragm (202). At the end of the housing (200), leads (212) transmit electrical signals from the internal microphone.

Figure 5:
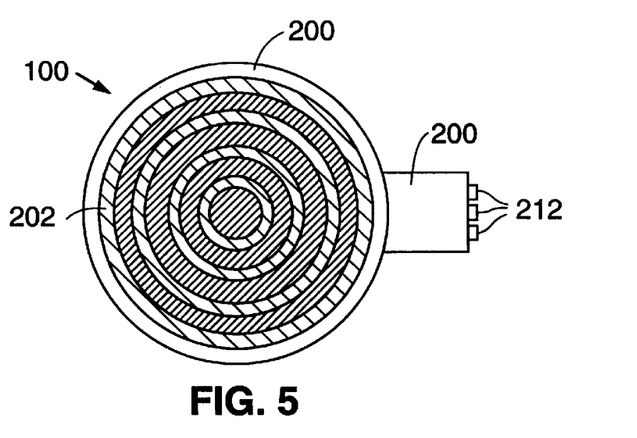
FIG. 5 shows a top view of one embodiment of a two-stage implantable microphone without a protective cover.

FIG. 5 shows a top view of one embodiment of a two-stage microphone without the protective cover. The differential shading in this Figure shows the bellows in the diaphragm.

Figure 6:
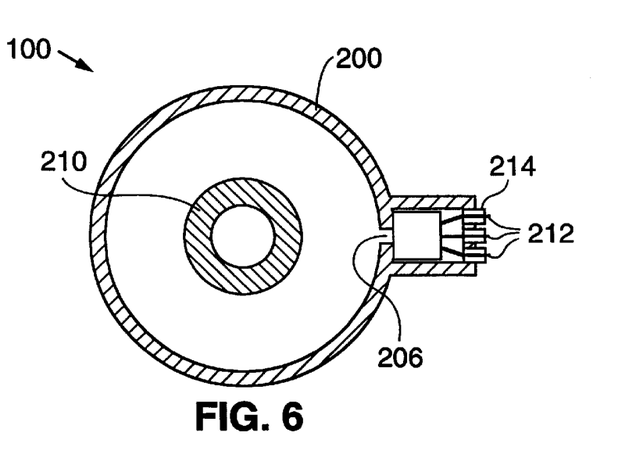
FIG. 6 shows a cross-sectional view of one embodiment of a two-stage implantable microphone transverse to the view of FIG. 2.

FIG. 6 shows a cross-sectional view of one embodiment of a two-stage implantable microphone transverse to the view of FIG. 3. An acoustic resistor (210) is located within the housing (200). As shown, the acoustic resistor may be tubular in shape. Additionally, there are three plates (214) that allow three leads (212) to pass from the transducer within the housing to the exterior. In this embodiment, the plates are brazened to hermetically seal the implantable microphone. The leads carry electrical signals that correspond to the bending and flexing of the diaphragm in response to sounds.

Figure 7A:
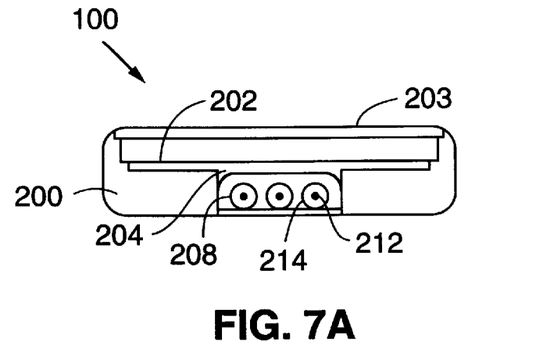
FIGS. 7A–7C show an alternative embodiment of two-stage microphones.
Figure 7B:
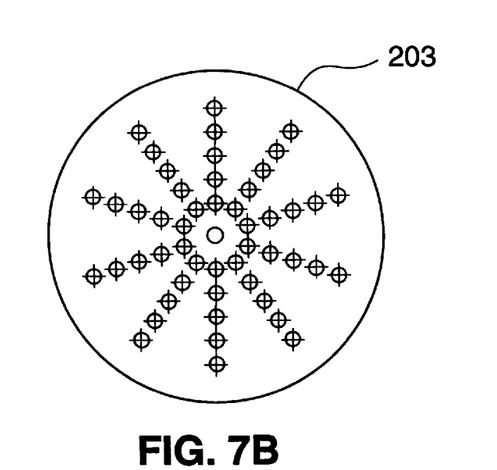
Figure 7C:
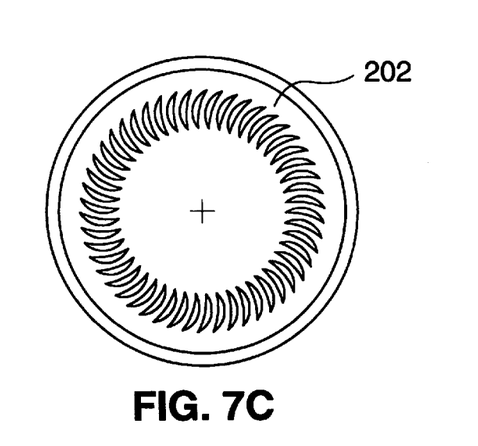

FIGS. 7A–7C show another embodiment of two-stage implantable microphones. The same reference numerals are utilized to indicate structures corresponding to similar structures in previous embodiments. In FIG. 7A, implantable microphone (100) includes a diaphragm (202), a protective cover (203), and a transducer (208).

FIG. 7B shows the protective cover with inlet ports chemically etched through the metallic protective cover. In a preferred embodiment, the protective cover is comprised of chemically etched titanium.

FIG. 7C shows the diaphragm containing chemically etched indentations. The indentations are etched partially through (e.g, halfway) the diaphragm, in order to increase the flexibility of the diaphragm. In one preferred embodiment, the protective cover is comprised of chemically etched titanium.

Various embodiments of the present invention have been tested in a variety of ways and have been found to provide excellent sound quality. Initially, the embodiments were tested in open air, utilizing a Fonix 6500 tester (Fryes Electronics) The open air tests were performed in order to generate baseline values for testing the implantable microphone embodiments at multiple frequencies. The implantable microphone embodiments were then tested in a Fonix tester containing physiological saline (i.e., 0.7% NaCl) or water. These tests were performed in order to simulate the placement of the implantable microphones in a body cavity. The implantable microphones were submerged at various depths, ranging from approximately 10–15 mm.

The implantable microphone embodiments were also tested within tissue from a pig cadaver, placed within a Fonix tester. In each test, implantable microphone was placed within a pocket in the pig tissue at a depth of approximately 10 mm. The pig tissue containing the microphone was then immersed in a saline bath, to simulate the conditions of implantation in soft tissue.

Comparisons of the output from the implantable microphone from the bath and pig tissue to the baseline open air test indicated that certain embodiments of the implantable microphone possessed good linearity and frequency response. Additionally, speech and music were played so that listeners could subjectively evaluate the implantable microphone under these the three conditions tested (i.e., open air, within the bath, and within pig tissue). These experiments confirmed that certain embodiments of the implantable microphones provide excellent audio characteristics.

It is further contemplated that the implantable microphone be used to monitor vital sounds, including but not limited to heart rate, blood flow, respiratory sounds (e.g., inspirational and expiration), intestinal movement, etc. In these embodiments, the implantable microphone may be of any size suitable for its intended use, although in preferred embodiments, the microphone is small (e.g., 2 mm×5 mm, or 3 mm×15 mm). In some embodiments, the microphone is implanted anywhere within any of the body cavities. In other embodiments, the microphone is placed under the skin (i.e., subcutaneous implantation). Importantly, subcutaneously implanted microphones may be implanted on an outpatient basis, and may be implanted at the physician's office, avoiding the necessity and cost of hospital admission. Thus, it is contemplated that the device and methods of the present invention be situated in a manner that the device functions at an optimal level. It is contemplated that the device be located in close proximity to the larynx or an organ to be monitored. It is contemplated that the exact positioning of the device will vary, depending upon each individual's anatomy. For "close proximity," all that is required is that the implantable microphone or other device be located sufficiently near the vocal cords or organ, etc. to be monitored, such that sounds from the vocal cords or organ may be detected and transmitted by the microphone.

While in most embodiments it is intended that the implantable microphone be used on a permanent basis, it is also contemplated that the microphones will be used on a temporary basis. For example, the device may be implanted and the vital sound may be monitored for a short time period, in order to provide useful diagnostic information. In particular, it is intended that the microphone be used to monitor heart sounds over time. In these embodiments it is further contemplated that the sounds be monitored by transmission of the sounds to a recording device that is either also implanted within the patient, present in the environment or attached to the person. This allows the physician to gather data over time, providing useful information related to the organ being monitored as it functions during either normal activity or during stress (e.g., strenuous physical activity). Thus, the implantable microphones of the present invention may be used for diagnostic and research purposes.

It is not intended that the present invention be limited to the embodiments described above. It is intended that various alternatives, modifications, and equivalents may be used. It is also intended that the present invention is equally applicable to various uses. For example, the implantable microphone and audio processor (i.e., the other components of the system) may be separate, or they may be integrated into one device. Thus, the descriptions are not intended to limit the scope of the invention.

DEFINITIONS

The larynx is the organ of voice. It is comprised of the air passage between the lower pharynx and the trachea, containing the vocal cords and is formed by cartilages (i.e., the thyroid, cricoid, epiglottis, and the paired arytenoid, corniculate, and cuneiform cartilages).

The laryngopharynx is the portion of the pharynx located below the upper edge of the epiglottis, and opens into the larynx and esophagus.

The pharynx is the area commonly referred to as the "throat." This area encompasses the musculomembranous cavity located behind the nasal cavities, mouth, and larynx, and the esophagus.

The nasopharynx is the portion of the pharynx that is located above the soft palate. As used herein, the term "subject" refers to a human or other animal. It is intended that the term encompass patients, such as vocally-impaired patients, as well as inpatients or outpatients with which the present invention is used as a diagnostic or monitoring device. It is also intended that the present invention be used with healthy subjects (i.e., humans and other animals that are not vocally-impaired, nor suffering from disease). Further, it is not intended that the term be limited to any particular type or group of humans or other animals.

As used herein, the term "vocal stimulator" refers to any device or method that assists in vocalization of vocally-impaired patients. For example, the term encompasses devices that electrically, mechanically or electromechanically stimulate the vocal cords in a manner such that vocalization results. It also encompasses devices and methods that simulate vocal sounds.

As used herein, the term "biocompatible" refers to any substance or compound that has minimal (i.e., no significant difference is seen compared to a control), if any, effect on the surrounding tissue. For example, in some embodiments of the present invention, the enclosure comprises a biocompatible housing containing a microphone; the housing itself has a minimal effect on the tissues surrounding the housing and on the subject after the implantable microphone is surgically placed. It is also intended that the term be applied in references to the substances or compounds utilized in order to minimize or avoid an immunologic reaction to the housing or other aspects of the invention. Particularly preferred biocompatible materials include, but are not limited to titanium, gold, platinum, sapphire, and ceramics.

As used herein, the term "implantable" refers to any device that may be surgically implanted in a patient. It is intended that the term encompass various types of implants. For example, the device may be implanted within a body cavity (e.g., thoracic or abdominal cavities), under the skin (i.e., subcutaneous), or placed at any other location suited for the use of the device. An implanted device is one that has been implanted within a subject, while a device that is "external" to the subject is not implanted within the subject (i.e., the device is located externally to the subject's skin).

As used herein, the term "hermetically sealed" refers to a device or object that is sealed in a manner that liquids or gas located outside the device is prevented from entering the interior of the device, to at least some degree. It is intended that the sealing be accomplished by a variety of means, including but not limited to mechanical, glue or sealants, etc. In particularly preferred embodiments, the hermetically sealed device is made so that it is completely leak-proof (i.e., no liquid or gas is allowed to enter the interior of the device at all).

As used herein, the term "reproduction of sound" refers to the reproduction of sound information from an audiofrequency source of electrical signals. It is intended that the term encompass complete sound reproduction systems (i.e., comprising the original source of audio information, preamplifier, and control circuits, audiofrequency power amplifier[s] and loudspeaker[s]). It is intended that the term encompass monophonic, as well as stereophonic sound reproduction, including stereophonic broadcast transmission. In some embodiments, a sound reproduction system composed of high-quality components, and which reproduces the original audio information faithfully and with very low noise levels, is referred to as a "high-fidelity" system (hi-fi). As used herein, the term "audio processor" refers to any device or component that processes sound for any purpose.

As used herein, the term "acoustic wave" and "sound wave" refer to a wave that is transmitted through a solid, liquid, and/or gaseous material as a result of the mechanical vibrations of the particles forming the material. The normal mode of wave propagation is longitudinal (i.e., the direction of motion of the particles is parallel to the direction of wave propagation), the wave therefore consists of compressions and rarefactions of the material. It is intended that the present invention encompass waves with various frequencies, although waves falling within the audible range of the human ear (e.g., approximately 20 Hz to 20 kHz). Waves with frequencies greater than approximately 20 kHz are "ultrasonic" waves.

As used herein, the term "frequency" (v or $f$) refers to the number of complete cycles of a periodic quantity occurring in a unit of time. The unit of frequency is the "hertz," corresponding to the frequency of a periodic phenomenon that has a period of one second. Table 1 below lists various ranges of frequencies that form part of a larger continuous series of frequencies. Internationally agreed radiofrequency bands are shown in this table. Microwave frequencies ranging from VHF to EHF bands (i.e., 0.225 to 100 GHz) are usually subdivided into bands designated by the letters, P, L, S, X, K, Q, V, and W.

TABLE 1

Radiofrequency Bands

| Frequency | Band | Wavelength |
| --- | --- | --- |
| 300 to 30 GHz | Extremely High Frequency (EHF) | 1 mm to 1 cm |
| 30 to 3 GHz | Superhigh Frequency (SHF) | 1 cm to 10 cm |
| 3 to 0.3 GHz | Ultrahigh Frequency (UHF) | 10 cm to 1 m |
| 300 to 30 MHz | Very High Frequency (VHF) | 1 m to 10 m |
| 30 to 3 MHz | High Frequency (HF) | 10 m to 100 m |
| 3 to 0.3 MHz | Medium Frequency (MF) | 100 m to 1000 m |
| 300 to 30 kHz | Low Frequency (LF) | 1 km to 10 km |
| 30 to 3 kHz | Very Low Frequency (VLF) | 10 km to 100 km |

As used herein, the term "gain," measured in decibels, is used as a measure of the ability of an electronic circuit, device, or apparatus to increase the magnitude of a given electrical input parameter. In a power amplifier, the gain is the ratio of the power output to the power input of the amplifier. "Gain control" (or "volume control") is a circuit or device that varies the amplitude of the output signal from an amplifier.

As used herein, the term "decibel" (dB) is a dimensionless unit used to express the ratio of two powers, voltages, currents, or sound intensities. It is 10× the common logarithm of the power ratio. If two power values (P1 and P2) differ by n decibels, then $n = 10 \log_{10}(P2/P1)$, or $P2/P1 = 10^{n/10}$. If P1 and P2 are the input and output powers, respectively, of an electric network, if n is positive (i.e., P2>P1), there is a gain in power. If n is negative (i.e., P1>P2), there is a power loss.

As used herein, the terms "carrier wave" and "carrier" refer to a wave that is intended to be modulated in modulated, or, in a modulated wave, the carrier-frequency spectral component. The process of modulation produces spectral components termed "sidebands" that fall into frequency bands at either the upper ("upper sideband") or lower ("lower sideband") side of the carrier frequency. A sideband in which some of the spectral components are greatly attenuated is referred to a "vestigial sideband." Generally, these components correspond to the highest frequency in the modulating signals. A single frequency in a sideband is referred to as a "side frequency," while the "baseband" is the frequency band occupied by all of the transmitted modulating signals.

As used herein, the term "modulation" is used in general reference to the alteration or modification of any electronic parameter by another. For example, it encompasses the process by which certain characteristics of one wave (the "carrier wave" or "carrier signal") are modulated or modified in accordance with the characteristic of another wave (the "modulating wave"). The reverse process is "demodulation," in which an output wave is obtained that has the characteristics of the original modulating wave or signal. Characteristics of the carrier that may be modulated include the amplitude, and phase angle. Modulation by an undesirable signal is referred to as "cross modulation," while "multiple modulation" is a succession of processes of modulation in which the whole, or part of the modulated wave from one process becomes the modulating wave for the next.

As used herein, the term "demodulator" ("detector") refers to a circuit, apparatus, or circuit element that demodulates the received signal (i.e., extracts the signal from a carrier, with minimum distortion). "A modulator" is any device that effects modulation.

As used herein, the term "dielectric" refers to a solid, liquid, or gaseous material that can sustain an electric field and act as an insulator (i.e., a material that is used to prevent the loss of electric charge or current from a conductor, insulators have a very high resistance to electric current, so that the current flow through the material is usually negligible).

As used herein, the term "electronic device" refers to a device or object that utilizes the properties of electrons or ions moving in a vacuum, gas, or semiconductor. "Electronic circuitry" refers to the path of electron or ion movement, as well as the direction provided by the device or object to the electrons or ions. A "circuit" or "electronics package" is a combination of a number of electrical devices and conductors that when connected together, form a conducting path to fulfill a desired function, such as amplification, filtering, or oscillation. Any constituent part of the circuit other than the interconnections is referred to as a "circuit element." A circuit may be comprised of discrete components, or it may be an "integrated circuit." A circuit is said to be "closed," when it forms a continuous path for current. It is contemplated that any number of devices be included within an electronics package. It is further intended that various components be included in multiple electronics packages that work cooperatively to amplify sound. In some embodiments, the "vocal electronics" package refers to the entire system used to improve and/or amplify sound production.

As used herein, the term "electret" refers to a substance that is permanently electrified, and has oppositely charged extremities.

As used herein, the term "amplifier" refers to a device that produces an electrical output that is a function of the corresponding electrical input parameter, and increases the magnitude of the input by means of energy drawn from an external source (i.e., it introduces gain). "Amplification" refers to the reproduction of an electrical signal by an electronic device, usually at an increased intensity. "Amplification means" refers to the use of an amplifier to amplify a signal. It is intended that the amplification means also includes means to process and/or filter the signal.

As used herein, the term "receiver" refers to the part of a system that converts transmitted waves into a desired form of output. The range of frequencies over which a receiver operates with a selected performance (i.e., a known level of sensitivity) is the "bandwidth" of the receiver. The "minimal discernible signal" is the smallest value of input power that results in output by the receiver.

As used herein, the term "transmitter" refers to a device, circuit, or apparatus of a system that is used to transmit an electrical signal to the receiving part of the system. A "transmitter coil" is a device that receives an electrical signal and broadcasts it to a "receiver coil." It is intended that transmitter and receiver coils may be used in conjunction with centering magnets which function to maintain the placement of the coils in a particular position and/or location.

As used herein, the terms "speaker" and "loudspeaker" refer to electroacoustic devices that convert electrical energy into sound energy. The speaker is the final unit in any sound reproducer or acoustic circuit of any broadcast receiver. It is not intended that the present invention be limited to any particular type of speaker. For example, the term encompasses loudspeakers including but not limited to magnetic, cone, horn, crystal, magnetorestriction, magnetic-armature, electrostatic, labyrinth speakers. It is also intended that multiple speakers of the same or different configurations will be used in the present invention.

As used herein, the term "microphone" refers to a device that converts sound energy into electrical energy. It is the converse of the loudspeaker, although in some devices, the speaker-microphone may be used for both purposes (i.e., a loudspeaker microphone). Various types of microphones are encompassed by this definition, including carbon, capacitor, crystal, moving-coil, and ribbon embodiments. Most microphones operate by converting sound waves into mechanical vibrations that then produce electrical energy. The force exerted by the sound is usually proportional to the sound pressure. In some embodiments, a thin diaphragm is mechanically coupled to a suitable device (e.g., a coil). In alternative embodiments the sound pressure is converted to electrical pressure by direct deformation of suitable magnetorestrictive or piezoelectric crystals (e.g., magnetorestriction and crystal microphones).

As used herein, the term "transducer" refers to any device that converts a non-electrical parameter (e.g. sound, pressure or light), into electrical signals or vice versa. Microphones are one electroacoustic transducers.

As used herein, the term "resistor" refers to an electronic device that possess resistance and is selected for this use. It is intended that the term encompass all types of resistors, including but not limited to, fixed-value or adjustable, carbon, wire-wound, and film resistors. The term "resistance" (R; ohm) refers to the tendency of a material to resist the passage of an electric current, and to convert electrical energy into heat energy.

As used herein, the term "reset" refers to the restoration of an electrical or electronic device or apparatus to its original state following operation of the equipment.

As used herein, the term "residual charge" refers to the portion of a charge stored in a capacitor that is retained when the capacitor is rapidly discharged, and may be subsequently withdrawn. Although it is not necessary to use the present invention, it is hypothesized that this results from viscous movement of the dielectric under charge causing some of the charge to penetrate the dielectric and therefore, become relatively remote from the plates; only the charge near the plates is removed by rapid discharge.

As used herein, the term "current" refers to the rate of flow of electricity. The current is usually expressed in amperes; the symbol used is "I."

As used herein, the term "residual current" refers to a current that flows for a short time in the external circuit of an active electronic device after the power supply to the device has been turned off. The residual current results from the finite velocity of the charge carriers passing through the device. The term "active" is used in reference to any device, component or circuit that introduces gain or has a directional function. An "active current," "active component," energy component," "power component" or "in-phase component of the current" refers to the component that is in phase with the voltage, alternative current, and voltage being regarded as vector quantities. The term "passive" refers to any device, component or circuit that does not introduce gain, or does not have a directional function. It is intended that the term encompass pure resistance, capacitance, inductance, or a combination of these.

As used herein, the terms "power source" and "power supply" refer to any source of electrical power in a form that is suitable for operating electronic circuits. Alternating current power may be derived either directly or by means of a suitable transformer. "Alternating current" refers to an electric current whose direction in the circuit is periodically reversed with a frequency $f$, that is independent of the circuit constants. Direct current power may be supplied from various sources, including, but not limited to batteries, suitable rectifier/filter circuits, or from a converter. "Direct current" refers to an unidirectional current of substantially constant value. The term also encompasses embodiments that include a "bus" to supply power to several circuits or to several different points in one circuit. A "power pack" is used in reference to a device that converts power from an alternating current or direct current supply, into a form that is suitable for operating electronic device(s).

EXPERIMENTAL

The following examples are provided in order to demonstrate and flirter illustrate certain preferred embodiments and aspects of the present invention and are not to be construed as limiting the scope thereof.

In the experimental disclosure which follows, the following abbreviations apply: dB (decibel); kHz (kilohertz); SPL (sound pressure level); Frye Electronics (Frye Electronics, Inc., Tigard, Oreg.); Realistic (Realistic, Radio Shack, Ft. Worth, Tex.); and Knowles (Knowles Electronics, Itasca, Ill.).

EXAMPLE 1

Testing Of Implantable Microphones

Figure 9:
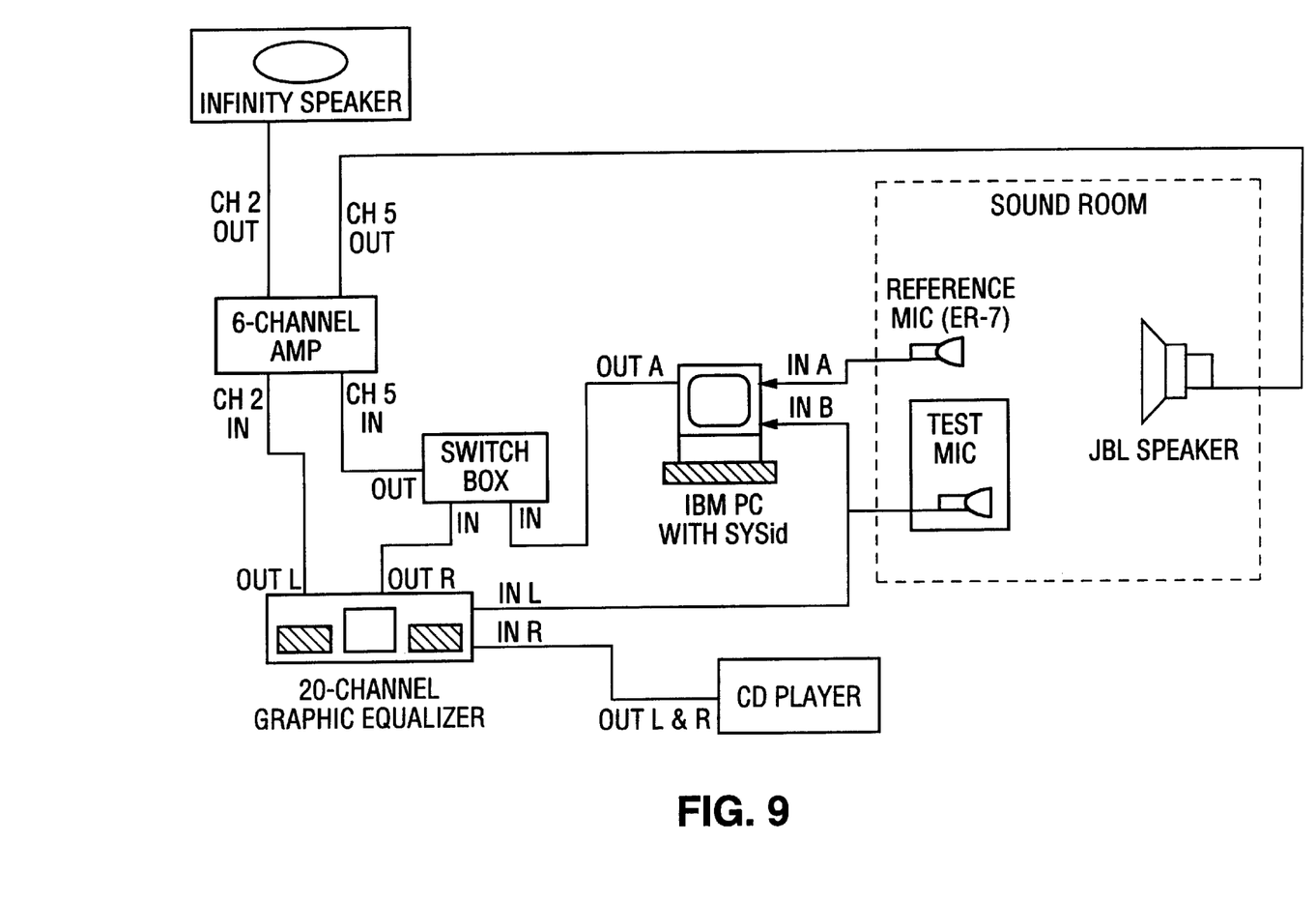
FIG. 9 provides a diagram of the set-up and connections used in the system used to test embodiments of the present invention.

In this Example, various implantable microphone prototypes were tested under controlled conditions. FIG. 9 provides a diagram of the set-up and connections used. In these experiments, the test equipment was placed on tripods and arranged in a manner such that the distance from the microphones to the speaker was approximately 12 inches. The microphones were vertically and horizontally centered with the speaker, and the distance to the floor of the sound room was approximately 50 inches.

The software/testing configuration was set up as diagrammed in FIG. 9. The SYSid Audio Band Measurement and Analysis System was loaded into the computer. For every microphone configuration tested, a swept sine wave chirp was emitted from the speaker (JBL) at a level of approximately 90 dB SPL, and the response of the microphone was plotted as dB (relative to the response of the ER-7 reference microphone) vs frequency, from 0.1 to 10 kHz. Response graphs were printed directly from the computer screen, and saved to memory in ASCII. Individual test configuration parameters remained constant throughout the testing, and were captured at the top of every printed graph.

Figure 10:
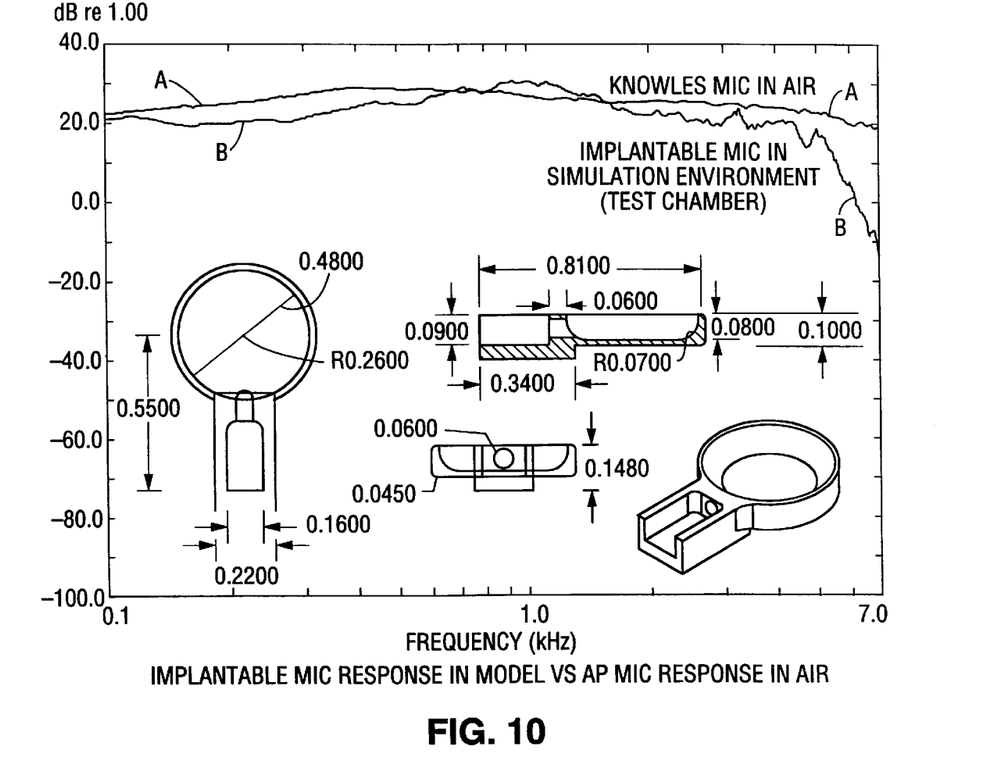
FIG. 10 is a graph showing the performance of one implantable microphone embodiment.

FIG. 10 is a graph showing the performance of one embodiment of an implantable microphone of the present invention. This graph also shows the dimensions and shape of the microphone. In this Figure, the frequency range is 0.1 to 7.0 KHz. Also in this Figure, line A shows the results for the ER-7 reference microphone tested in open air, while line B shows the results for the implantable microphone tested in a Fonix box. As shown in this Figure, the implantable microphone exhibited a good frequency response, with good voltage output. In addition, normal listening levels were good for this implantable microphone embodiment. On this graph, the dB level relative to one volt (1 v) at 0 db. Overall, the graph shows the various from one volt (1 v) at 0 dB in dB.

Twelve microphones were tested in this Example. The first transducer used in the microphone was an EM 9468 (Knowles). The dimensions of this microphone were 30 mm in diameter and 2.5 mm thickness. The microphone was housed in two 0.75 mm flexible plastic pieces, separated by 1.5 mm silicone tubing, coated in plastidip and epoxy. The sound quality of this microphone prior to assembly within the housing was good for speech and music. However, the sound quality of the completed microphone assembly was compromised, and the voltage output was low. The sound quality worsened to a very muddy, hollow sound, when the microphone assembly was placed in water.

The second implantable microphone tested used an EE 296 (Knowles) transducer, and was 31–34 mm in diameter and 2 mm thickness. The transducer was housed within a 0.5 mm titanium teardrop-shaped housing, with walls separated by an array of 0.02 inch silicone tubing. The sound quality of the transducer prior to assembly within the housing was good. However, the assembled implantable microphone sounded weak, "tinny" and needed much more amplitude to drive the speakers. When tested in water, the microphone assembly quickly flooded due to a breach in the housing coating. However, the sound quality was good prior to completely flooding.

The third implantable microphone used an EM 9468 (Knowles) as the transducer, and was 36 mm diameter and 6.0 mm thickness. This microphone was placed within a plastic housing with one side covered with Mylar (0.02 mm thickness). Prior to assembly within the housing, the microphone sound quality was great for speech and noise. However, after assembly, the microphone sound quality was poor, with too much bass, with limited high end frequency production, and a large degree of distortion. When tested in water, the microphone sounded somewhat better at a submersion depth of approximately 15 mm, although the sound still had too much bass, with almost no high frequencies.

The fourth implantable microphone used an EM 9468 (Knowles) transducer, and was 25 mm diameter, and 1.9 mm thickness. The microphone was housed within 0.3 inch silicone tubing, wrapped and sealed in a circle configuration, with the microphone sealed in epoxy. As with the other tests, the microphone alone sounded great in the box. The assembled microphone also sounded good, but the completely assembled device had a poor frequency response.

The fifth implantable microphone tested used an FK 496 (Knowles) transducer, and measured 40 mm×20 mm, and 1.9 mm in thickness. The housing for this microphone consisted of 35 mm tubes joined to produce one tube. Prior to assembly within the housing, the microphone sound quality was good for speech and noise. After assembly, the sensitivity was decreased, although the high and mid-range sound quality was good. However, "sea shell" resonance was very noticeable. In the submersion test, the assembled microphone sounded good until it flooded (10–15 mm water depth).

The sixth implantable microphone tested used an F0196 (Knowles) transducer, and measured 15 mm by 10 mm, and 2.5 mm in thickness. The housing was a titanium housing containing 0.03 inch silicone tubing, and coated in plastidip. Prior to assembly, the transducer sound quality was very good. After assembly into the microphone, extensive amplification was needed in order for the microphone to work. Overall, the frequency response was poor, the signal was hard to hear (i.e., the output was very low).

The seventh implantable microphone tested used an FE 296 (Knowles) transducer, and measured 45×25 mm, and 5.0 mm in thickness. The housing for this microphone consisting of five 4.8 mm, thin-walled polyvinyl tubes installed in a rubber bladder. The microphone was installed at the opening. Prior to assembly, the microphone sound quality was very good. After assembly, the bass was very good, although there were no high sounds, and the lows were muddy in quality. When tested underwater, there were no high or mid-range sounds, and there was a large degree of distortion.

The eighth implantable microphone tested used an 8946 (Knowles) transducer. The housing consisted of three distally secured 0.03 inch silicone tubes of 20 mm, 10 mm and 15 mm. Prior to assembly, the microphone sound quality was very good, and was unaltered after the tubes were installed. The "sea shell" resonance was most noticeable on the 20 mm, and least on the shortest (i.e., 10 mm). The sound quality was good when the microphone was submerged, although the signal was weak.

The ninth implantable microphone tested used an RS 270-0928 (Realistic) transducer, and measured 12 mm, and 12 mm in thickness. The microphone was installed with 0.02 inch silicone tubing with a 0.09 mm titanium housing, sealed in plastidip. Prior to assembly, the microphone had a noticeable hiss. After assembly, the microphone sound quality was good, with good low, mid and high-range sound quality. When submerged in 10–15 mm water, the microphone sound quality was also good.

The tenth implantable microphone tested used an RS 270-0921 (Realistic) transducer, and measured 12 mm diameter, and 12 mm thickness. The microphone was installed with 0.03 inch silicone tubing and a titanium housing, and sealed in plastidip. Prior to assembly, the microphone sound quality was acceptable, but there was noticeably more hiss than the Knowles microphones used previously. After assembly, the microphone sound quality was good, both in air and when submerged in water.

The eleventh microphone tested was an FE 296 (Knowles), of 12 mm in diameter, and 3.3 mm in thickness. The microphone was installed within a 0.02 mm housing, between two thick, stiff surfaces composed of titanium. Prior to assembly, the microphone sound quality was good. The sound quality was also very good after assembly. When submerged, the sound quality was better than all of the previously tested microphones. However, the housing leaked.

The twelfth microphone tested was an FE 296 (Knowles), of 20 mm in diameter and 4.5 mm thickness. The microphone was installed with 0.03 inch tubing held between two stiff plates of medical grade silicone tubing. Prior to assembly, as well as after assembly, the microphone sound quality was very good. When submerged, the microphone sound quality was particularly good.

Figure 11:
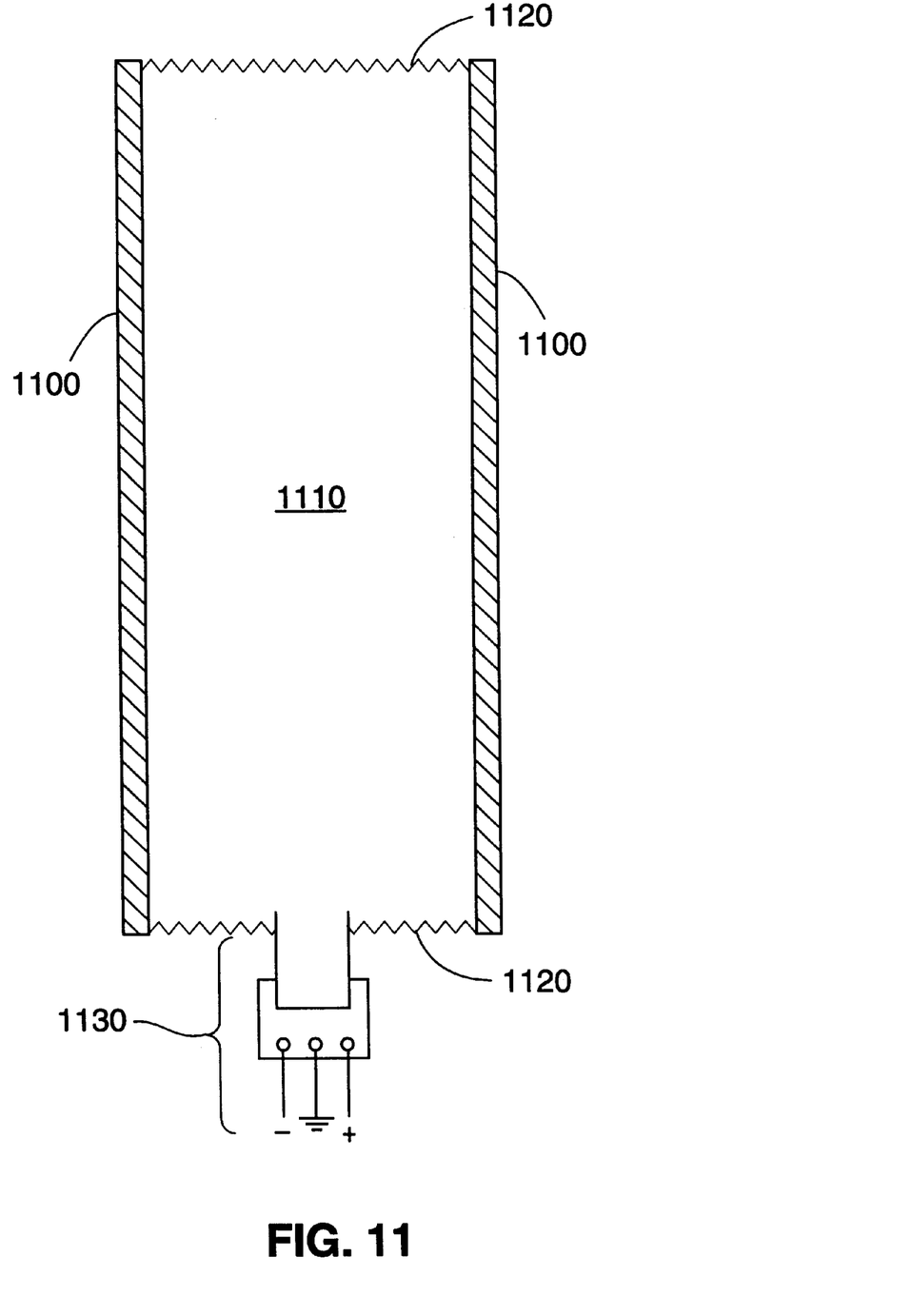
FIG. 11 shows one embodiment of the present invention.

These results indicated that the FE 296 (Knowles) microphone of 20 mm in diameter and 4.5 mm thickness installed between two stiff plates produced the best sound quality (FIG. 11). These results also indicated that the implantable microphones of the present invention may be produced, so as to maximize displacement of electret microphone diaphragms. This was accomplished by using two stiff surfaces, with a relatively "floppy" bellow or spring device (e.g., silicone tubing) placed between the two stiff surfaces. The frequency response of the microphone can be adjusted by changing the tension or stiffness (i.e., floppiness) of the bellows or springs, or by changing the electret microphone used. The sensitivity of the implantable microphone was adequate and sound quality was good.

FIG. 11 shows one embodiment of the implantable microphone of the present invention, corresponding to the twelfth microphone tested. To increase the sensitivity of the system, the stiffness of the plates (1100) may be maximized, the surface of the plates may be maximized, or the area between the plates (i.e., the chamber) may be minimized (1110). To maximize low frequencies, the bellows (1120) may be loosened, or an electret microphone (1130) with low frequency emphasis may be selected. For example, the electret microphone (1130) chosen may be selected based on its frequency response capabilities, to enhance the overall frequency responses of the entire implantable microphone system.

From the above, it is clear that the present invention provides and methods for the use of preparation of implantable microphones effective in the amplification of voice and other sounds. All publications and patents mentioned in the above specification are herein incorporated by reference. Various modifications and variations of the described method and system of the invention will be apparent to those skilled in the art without departing from the scope and spirit of the invention.

What is claimed is:

1. A method for amplifying speech comprising the steps of:
    a) providing:
        i) a subject, and
        ii) a two-stage implantable microphone for producing an electronic signal responsive to said subject's vocalizations; and
    b) implanting said implantable microphone within said subject.

2. A method for amplifying speech comprising the step of providing:
    i) a subject;
    ii) a two-stage implanted microphone for producing an electronic signal responsive to said subject's vocalizations;
    iii) an amplifying means for amplifying said electronic signal to produce an amplified signal; and
    iv) a broadcasting means for broadcasting said amplified signal to produce a broadcast signal.

3. The method of claim 2, wherein said amplifying means further comprises a filtering means.

4. The method of claim 3, wherein said amplifying means further comprises a processing means.

5. The method of claim 2, further comprising a modulating means, wherein said amplified signal is modulated; and a demodulating means, wherein said broadcasted signal is demodulated.

6. The method of claim 3, wherein said modulated signal is selected from the group consisting of AM, FM, and bass band.

7. The method of claim 2, wherein said broadcasting means comprises a transmitter coil, a receiving coil, an amplified, and at least one speaker.

8. The method of claim 2, wherein said transmitter coil is implanted within said subject.

9. The method of claim 2, wherein said receiving coil is external.

10. The method of claim 2, wherein said speaker is selected from the group consisting of a room speaker and a personal speaker.

11. The method of claim 2, wherein said implanted microphone is implanted in close proximity to said subject's vocal cords.

12. The method of claim 2, wherein said implanted microphone is hermetically sealed.

13. A method for amplifying speech comprising:
   a) producing an electronic signal responsive to the vocalizations of a subject using a microphone implanted within said subject;
   b) amplifying said electronic signal using an amplifying means comprising a processing means, to produce an amplified signal; and
   c) broadcasting said amplified signal using a broadcasting means, to produce a broadcasted signal.

14. The method of claim 13, wherein said amplifying means further comprises a filtering means.

15. The method of claim 13, further comprising the steps of:
   d) modulating said amplified signal to produce a modulated signal; and
   e) demodulating said modulated signal.

16. The method of claim 15, wherein said modulated signal is selected from the group consisting of AM, FM and bass band.

17. The method of claim 13, wherein said broadcasting means comprises a transmitter coil, a receiving coil, an amplifier, and at least one speaker.

18. The method of claim 17, wherein said transmitter coil is implanted within said subject.

19. The method of claim 18, wherein said speaker is selected from the group consisting of a room speaker and a personal speaker.

20. The method of claim 17, wherein said receiving coil is external.

21. The method of claim 13, wherein said microphone is a two-stage microphone comprising a first stage that allows the selection of microphone frequency response and a second stage that allows the selection of microphone sensitivity.

* * * * *